(12) United States Patent
Quaet-Faslem et al.

(10) Patent No.: US 8,134,366 B2
(45) Date of Patent: Mar. 13, 2012

(54) MEDICAL DIAGNOSTIC DEVICE COMPRISING AN OPERATING ELEMENT FOR CONTROLLING SYSTEM COMPONENTS

(75) Inventors: Philipp Quaet-Faslem, München (DE); Judith Regn, Nürnberg (DE); Elizabeth Rogers, Forchheim (DE); Reiner Staab, Baiersdorf (DE); Susanne Staab, legal representative, Baiersdorf (DE); Klaus Thormann, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 1124 days.

(21) Appl. No.: 11/922,160

(22) PCT Filed: Jun. 12, 2006

(86) PCT No.: PCT/EP2006/063096
§ 371 (c)(1),
(2), (4) Date: Dec. 13, 2007

(87) PCT Pub. No.: WO2006/134089
PCT Pub. Date: Dec. 21, 2006

(65) Prior Publication Data
US 2009/0062638 A1    Mar. 5, 2009

(30) Foreign Application Priority Data
Jun. 13, 2005 (DE) .................. 10 2005 027 358

(51) Int. Cl.
*G01V 3/00* (2006.01)
(52) U.S. Cl. ......................................... 324/318; 378/62
(58) Field of Classification Search .................. 324/318, 324/322; 345/156, 158, 184; 378/62
See application file for complete search history.

(56) References Cited

U.S. PATENT DOCUMENTS

| | | | |
|---|---|---|---|
| 5,059,958 A * | 10/1991 | Jacobs et al. ................... | 345/158 |
| 5,883,615 A * | 3/1999 | Fago et al. ..................... | 345/156 |
| 2003/0004497 A1 | 1/2003 | Chappuis | |

FOREIGN PATENT DOCUMENTS

| | | |
|---|---|---|
| DE | 42 24 246 C1 | 8/1993 |
| EP | 0 506 172 A2 | 9/1992 |
| JP | 11285491 A | 10/1999 |

* cited by examiner

Primary Examiner — Louis Arana

(57) ABSTRACT

The invention relates to a medical diagnostic device comprising an operating element for controlling system components of the medical diagnostic device, said device comprising at least one operating lever which is embodied in such a way that it has at least one feature which is characteristic of the associated system component and is, for example, designed in such a way that it is congruent to the system component. In this way, the operating lever has a form adapted to that of the real system components or has the same form as said components.

19 Claims, 4 Drawing Sheets

MEDICAL DIAGNOSTIC DEVICE COMPRISING AN OPERATING ELEMENT FOR CONTROLLING SYSTEM COMPONENTS

CROSS REFERENCE TO RELATED APPLICATIONS

This application is the US National Stage of International Application No. PCT/EP2006/063096 filed Jun. 12, 2006 and claims the benefits thereof. The International Application claims the benefits of German application No. 10 2005 027 358.0 filed Jun. 13, 2005, both of the applications are incorporated by reference herein in their entirety.

FIELD OF THE INVENTION

The invention relates to a medical diagnostic device comprising an operating element for controlling system components of the medical diagnostic device with at least one operating lever. Such an operating element forms part of, for example, an X-ray diagnostic device for angiography systems, but also for card angiography systems, hereinafter referred to as angio systems, described in the Siemens prospectus "AXIOM Artis—Endovascular Procedures in the OR environment".

BACKGROUND OF THE INVENTION

Such angio systems contain different system components, in particular an electrically adjustable patient receiving table, an X-ray stand, a detector and an X-ray source. Before the start the start of examination, each of these system components must be adjusted to a position preset by the examination. In this process, the adjustment of the relevant system component usually takes place from a control panel that is placed in close proximity to a patient on the patient receiving table.

However, also during the course of a diagnosis or an intervention, the operation of an angio system requires the exact control of system movements and other system functions. In this process, the main concentration of the user is given to the patient or the live X-ray image of the patient as well as the handling of catheters and injections. The plurality of system components and functions to be controlled requires a plurality of operating elements. The operation is especially carried out in sterile manner, so that the operating elements are frequently covered by means of a plastic film. In addition, corresponding procedures are often carried out in a darkened room.

Such an X-ray diagnostic device, for example, well-known from DE 100 37 735 A1 is shown in FIG. 1, which has a C arm 2 rotatably mounted on an X-ray stand 1 and at the ends of which an X-ray emitter 3 and an X-ray image detector 4 are attached.

Instead of the X-ray stand 1 shown, it is also possible to use floor supports and/or ceiling supports. The C arm 2 can also be replaced by a so-called electronic C arm, in the case of which an electronic coupling of individual X-ray emitters 3 and X-ray image detectors 4 attached to a stand is carried out in each case.

The X-ray image detector 4 can be a rectangular or a quadratic, flat semiconductor detector, which is preferably made of amorphous silicon (aSi).

A patient receiving table 5 is positioned in the beam path of the X-ray emitter 3 for the admission of the patient to be examined. The patient receiving table 5 has a table leg 6, a supporting plate 7 and a control panel 8 applied thereto.

The current operation of angio systems especially takes place via a control panel 8 mounted on the patient receiving table 5, by using joysticks, knobs and a touchscreen as well as via a floor switch. System movements are activated in particular via joysticks. The activation of X-ray radiation mainly takes place by means of the floor switch. Several joysticks are provided, which in part only differ in size and quantity from the incorporated pushbuttons, as well as some pushbuttons and status LEDs. Depending on the examination program that is set, further functions and parameters for controlling system operations are displayed on the touchscreen in a dynamic manner.

FIG. 2 shows such a control panel 8 of an X-ray diagnostic device for controlling the system components shown in FIG. 1 such as for example for controlling the electrically adjustable patient receiving table 5, the X-ray stand 1, a collimator and an image system. In this process, a discrete operating element is in each case assigned to every system component, and is hooked into a rail mounted on the patient receiving table 5.

The discrete operating element 11 with a rotary control unit 12 is assigned to the patient receiving table 5, the discrete operating element 13 with an operating lever 14—mounted such that it can pivot—is assigned to the X-ray stand 1, the discrete operating element 15 with a group of operating levers 16—mounted such that they can pivot—is assigned to the collimator and a further operating element, namely a so-called touchscreen 17 with an additional operating lever 18, is assigned to the image system. When preparing for the examination, the system components are adjusted successively or simultaneously by means of the above-mentioned, discrete operating elements that can be operated manually to a specific position for the examination or to a specific parameter value for the examination.

In the event of a change in the operation between the discrete operating elements, it is necessary to move the hand from the one discrete operating element to another correspondingly discrete operating element. As a result of the spatial separation of the discrete operating elements 11, 13, 15 and 17, the user has to make visual contact with the control panel 8 in order to prevent the risk of incorrect operation because of inadvertent actuation of one of the operating levers 14, 16, 18 or the rotary control unit 12.

SUMMARY OF THE INVENTION

The object underlying the invention is thus to make available in the case of a medical diagnostic device as described in the introduction, in the above-mentioned situations, access to the desired system movement or system function reliably and quickly so that operation can take place without making visual contact and without the risk of incorrect operation.

The object is achieved in accordance with the invention in that the operating lever is embodied in such a way that it has at least one feature which is characteristic of the associated system component and is, for example, designed in such a way that it is congruent to the system component. This can be achieved in accordance with the invention in that the operating lever has a form adapted to the real system components or has the same form as said components.

In an advantageous manner, the movement directions and/or the color of the operating lever can correspond to the movement directions to be controlled of the real system components.

An advantageous identification is also guaranteed in the dark if the operating element has an illumination device, the light color of which corresponds to the color coding of the real system component to be controlled.

In accordance with the invention, the operating lever can be a joystick, a slide switch, a rotary switch or a foot operated switch.

Advantageously, the operating lever for controlling a C arm has a form adapted to that of a C arm. To this end, the operating lever can be equipped with an operating knob, being essentially shaped as a perpendicular round disk, which is cut off in the front region thereof.

In accordance with the invention, the surface of the disk can be designed in such a way that it has the form of elevations which are characteristic of a C arm.

In an advantageous manner, the operating lever for controlling a panel can have a form adapted to that of a panel, it being possible that the operating lever for controlling a panel can have an operating knob, the base surface of which being round, and in the case of which four perpendicular, unbowed elements can be arranged on the base surface at the edge, which are adapted to that of the panel edges.

Advantageously, the operating lever for controlling a patient receiving table has a form adapted to that of a patient receiving table, it being possible that it can have a toggle switch attached in a vertical position to the operating lever.

In the case of a diagnostic device with a control computer, which is connected to the system components to be controlled, it is advantageous if the control computer is embodied in such a way that a tone assigned to the control system is delivered as acoustic feedback, it being possible that another tone differing in tone pitch and/or tone color is assigned to each system component and/or each control command and it being possible that the control computer can have a tone generator.

BRIEF DESCRIPTION OF THE DRAWINGS

The invention is described in more detail below with reference to several exemplary embodiments and the associated drawings. They are as follows.

DETAILED DESCRIPTION OF THE INVENTION

Figure 1:
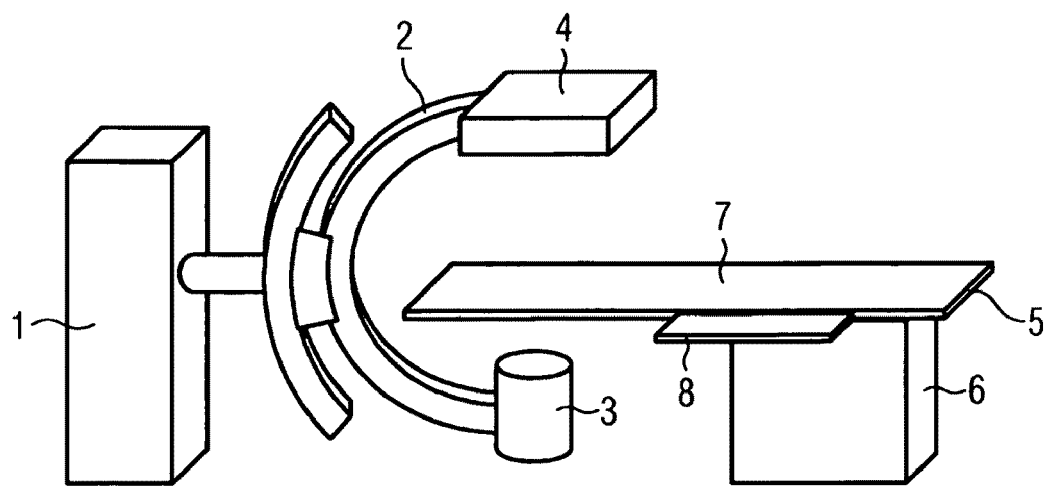
FIG. 1 a known X-ray diagnostic device.
Figure 2:
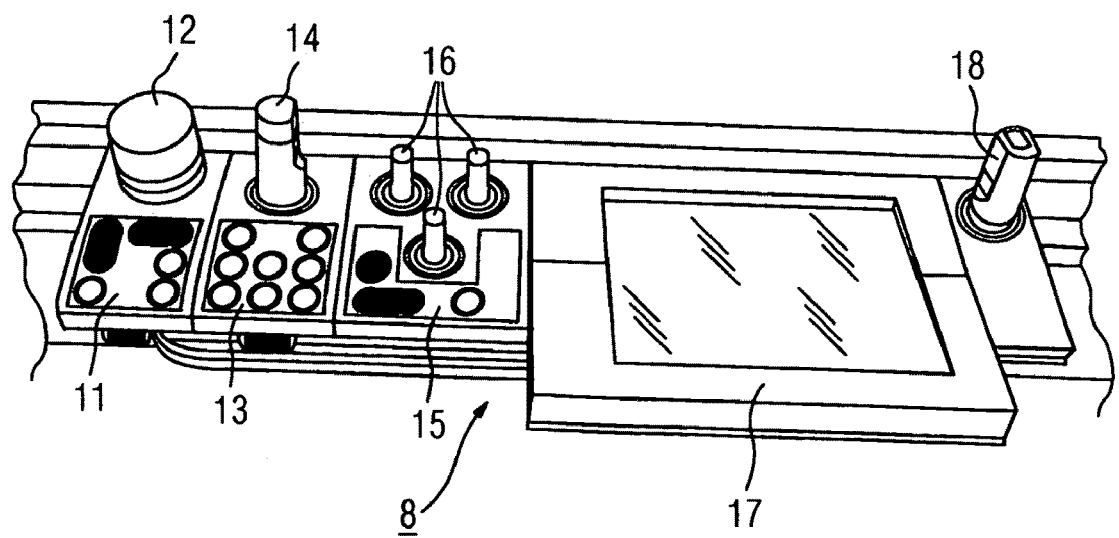
FIG. 2 a known control panel for controlling an X-ray diagnostic device in accordance with FIG. 1 by means of the discrete operating elements for an X-ray table, an X-ray stand, a collimator and an image system, FIG. 3 an X-ray diagnostic device in accordance with the invention, FIG. 4 an operating element for the gantry-style control of a C arm according to FIG. 3 in accordance with the invention, FIG. 5 an operating element for controlling a collimator in accordance with the invention, FIG. 6 an operating element for the patient receiving table according to FIG. 3 in accordance with the invention and FIG. 7 a foot operated switch for activating X-ray radiation.
Figure 3:
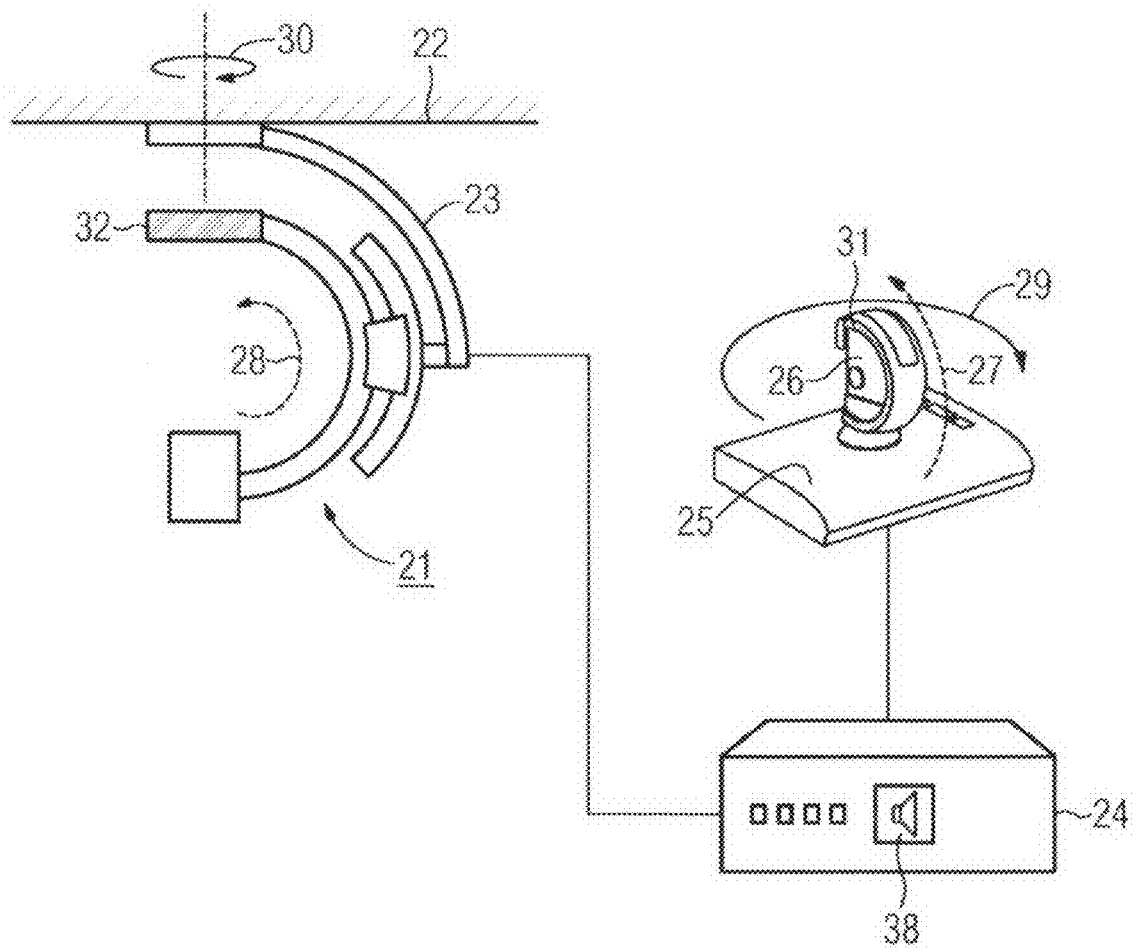

In FIG. 3, a C arm is shown as a system component 21. A ceiling support 23 for holding the system component 21 is attached to a ceiling 22 of for example an operating room. A control computer 24 is connected to said system component 21 in a known manner, an operating element 25 in turn being connected to said control computer 24. The operating element 25 has an operating lever 26, which has a form adapted to that of the C arm.

Figure 4:
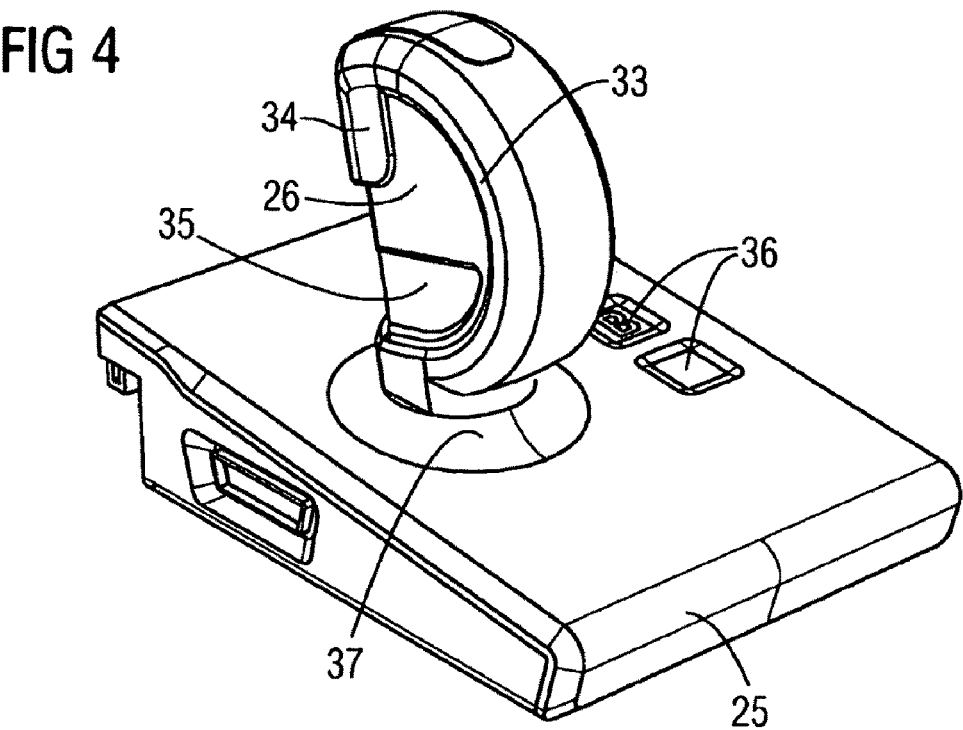

As can be seen in an even more accurate manner in FIG. 4, the operating lever 26 has a form adapted to that of the correspondingly assigned system component. It is essentially shaped as a perpendicular round disk, which is cut off in the front region thereof. The lateral surfaces of the disk are designed in such a way that they have the form of elevations which are characteristic of a C arm. As a result, it has an elevation 33 at the outer edge, which is to represent the C arm. An elevation 34 at the upper edge represents the X-ray emitter 3. A further elevation 35 at the lower part of the arm symbolizes for example the X-ray image detector 4. In addition, the operating element 25 has displays 36, which are equipped with codings and possibly with luminous areas. In this way it can for example be signaled, which system component is selected for example for the gantry-style control in the case of biplane operation and simply one operating element.

Therefore, by means of this operating lever 26, the movement of one of the system components 21 can be controlled. In this process, a color coding 32 on the system component 21 for example indicates which one of several operating elements (bi-plane operation) is assigned to this system component 21. This assignment is for example characterized by means of a color arc 31 or another coding. Therefore, both the system component 21 and the assigned operating element 25 have the same color.

For controlling the system component 21, if the operating lever 26 is for example swiveled in the direction of the dotted arrow 27, this brings about a swiveling action of the C arm in the direction of the dotted arrow 28, i.e., the X-ray system rotates around the patient, who would lie perpendicular to the plane of the drawing. On the other hand, if the operating lever 26 is rotated in the direction of the arrow 29, the system component 21 will then rotate about its vertical axis in the direction of the arrow 30. If the operating lever 26 is now tilted sideways, the C arm 2 of the system component 21 then rotates about its horizontal axis lying in the plane of the drawing which is not shown.

The control computer 24 is equipped with a tone generator 38, which generates a tone assigned to a control command as acoustic feedback. This is played back by a loudspeaker assigned to the X-ray device, it being possible that another tone differing in tone pitch and/or tone color is assigned to each system component and/or each control command. The loudspeaker can for example be arranged in the patient receiving table 5, in the system component 21 or in at least one operating element 25, 40, 50 or 60. It is important that it is located in the OR and is audibly heard by the person performing the examination.

Figure 5:
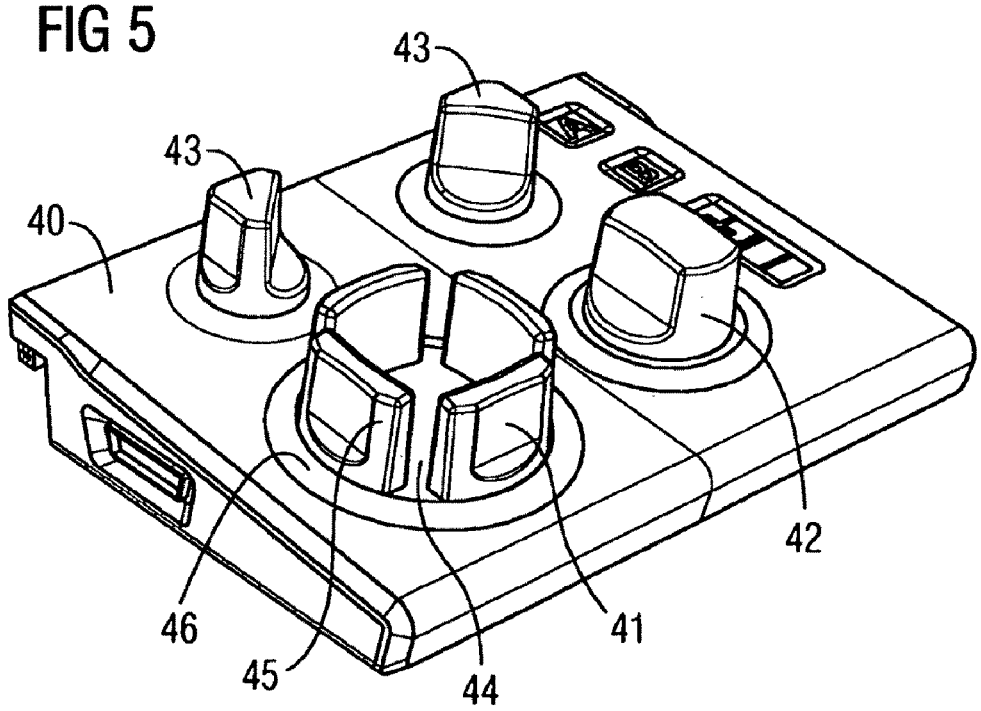

FIG. 5 shows an operating element 40 for adjusting collimators and filters. It is equipped with an operating lever 41 for a collimator, an operating lever 42 for a finger filter and with operating levers 43 for wedge filters. All the operating levers 41 to 43 can be swiveled in both directions and in addition rotated, on the basis of which a shifting in the directions of a plane as well as a rotation of the components can be brought about.

The operating knob for the operating lever 41 has a round base surface 44 on which four perpendicular, unbowed elements 45 are arranged at the edge, which are to represent the edges of the collimator. A narrow edge 46 is left around these elements on the base surface 44, which, as already described, can be equipped with a color coding.

The form of the operating lever 42 for a finger filter tapers towards the top at both sides so that it from the top feels, if it is touched blind, as though it were a rectangle. This is also the customary form of the finger filter. The two operating levers 43 for two wedge filters are embodied in such a manner that they taper towards the top from the circular base surface at three sides, it being possible that the hypotenuse is more strongly chamfered so that they result in isosceles triangles with rounded off points seen from above.

Figure 6:
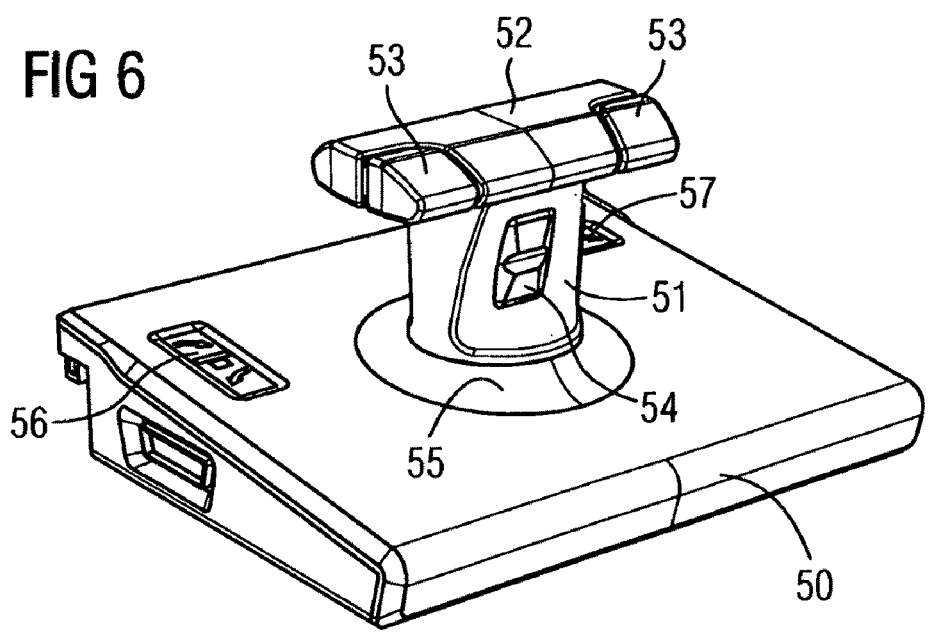

FIG. 6 shows an operating element 50 for the patient receiving table 5. It has an operating lever 51, onto and above which a rectangular head 52 which has a form adapted to that of a supporting plate is placed. Knobs 53 are provided on both sides of the head, which serve to release the table brake so that the patient receiving table 5 can be turned away to the side. This is necessary with the floor support in the case of certain examinations, for example, in very widely peripheral regions of interest and is advantageous in some areas for keeping the patient on the patient receiving table 5 and when returning said patient into the bed. In addition, a toggle switch 54 is attached to the operating lever 51, which serves to transport the patient receiving table 5 in an upward or in a downward direction.

The operating lever 51 has an edge 55 at the bottom which is either color coded or is held transparent and is illuminated from a light contained in the operating element 50.

If the operating element 50 is switched with a biplane device from the one plane to the other plane, then this is signaled by the change of the light. In this process, the light adopts the color which is applied in a clearly visible manner to the system (system component 21). It would in addition also be feasible that on changeover of the operating elements, the appropriate system becomes illuminated.

To the left of the operating lever 51 there is a knob 56 for tilting in a longitudinal direction and to the right a knob 57 for lateral tilting known as cradling.

By pressing or pulling the operating lever 51, the patient receiving table 5 moves in both directions. By the lateral movement of the operating lever 51, the patient receiving table 5 is shifted in a lengthwise direction toward the axis of the patient. Moving the patient receiving table 5 in an upward or in a downward direction is achieved by pressing the toggle switch 54 on the operating lever 51.

Figure 7:
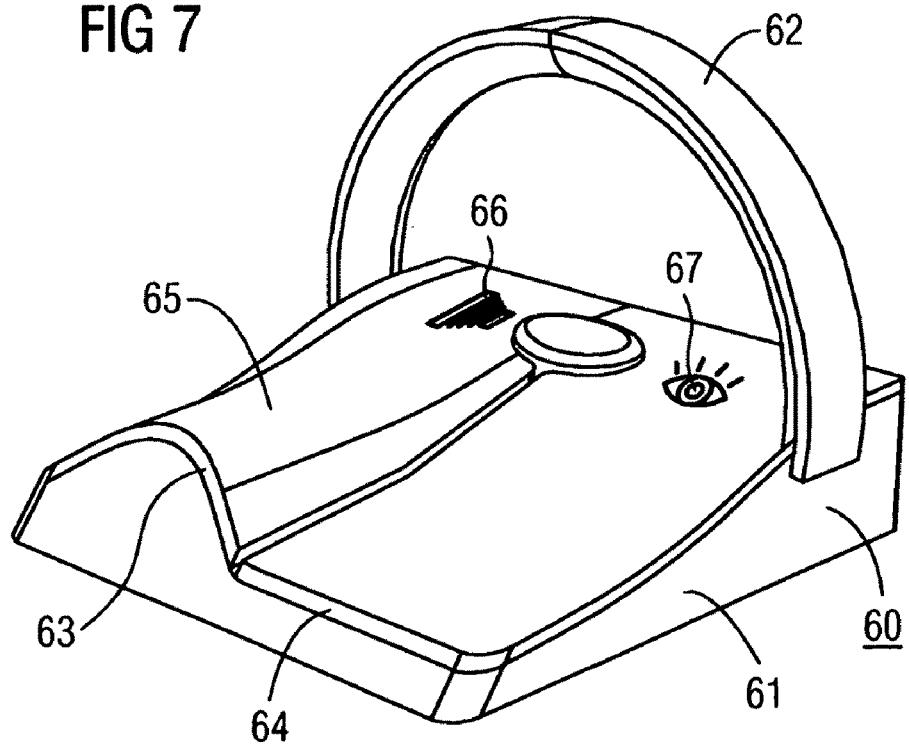

FIG. 7 shows a foot operated switch 60 for the activation of X-ray radiation. The foot operated switch 60 has a housing 61, on which there is a carrier grip 62. In the front region there is a switching element 63 for recording and a switching element 64 for transillumination (fluoroscopy). In order to distinguish between the two switching elements, the switching element 63 for recording has a curvature 65, whereas the switching element 64 for fluoroscopy is embodied in a flat manner. For visual distinction, the switching elements 63 and 64 are now characterized with the symbols 66 and 67.

The edges 37, 46 and 53 can either form the lower part of the operating lever 26, 41 and 51, or belong to the housing of the operating elements 25, 40 or 50. They can be color coded. However, in addition, they can be translucent and become illuminated from within by means of an illumination device, in particular in order to improve the ability to identify in the dark. In this process, the light of the illumination devices has different, switchable colors if necessary.

These ergonomic operating elements, by making a clear distinction, create the possibility for a safe system operation as an auxiliary function, without disturbing the major tasks carried out on the patient (for example, the handling of a catheter). The distinction is created by the form, color and light in the case of the operating elements as well as by means of auditive feedback. The different forms of the individual operating elements create a clear reference for the system function or the system component to be controlled. This reference in the case of important system components (for example, the C arm, panels, the patient receiving table), is achieved by using a form which is adapted to that of the real system components. The directions of motion of the operating elements correspond to the real directions of motion of the system components. This makes a safe identification and actuation of the operating element possible by feeling, i.e. also without looking closely or in the dark.

During darkness, the use of multi-colored light for the operating elements creates an improved ability to identify status information as well as the assigning of multiple existing identical components to the appropriate operating elements (for example, assigning the radiation pedal to the corresponding image planes, assigning panels). By using light and color, an ability to identify in the peripheral field of vision is also made possible in the illuminated area, so that the user can focus on the X-ray image or the patient. By means of auditive feedback, the user is informed about important system conditions and the execution of important functions without said user having to read this information visually from a monitor or an operating element.

By means of the embodiment of the operating elements in accordance with the invention, an improved tactile ability to identify, congruency of the form of real component and operating element, congruency of the directions of motion of real component and operating element, improved identification and the ability to assign operating elements in dark areas, improved ability to identify in the peripheral field of vision as well as a reduction in the concentration necessary for operating the system are achieved.

The invention claimed is:

1. A medical diagnostic device, comprising:
a control computer;
an operating element coupled to the control computer to effect at least one physical movement of a system component of the medical diagnostic device to change a spatial arrangement of the system component; and
an operating lever arranged on the operating element, the operating lever comprising a structural characteristic indicative of a form of the system component, wherein the structural characteristic of the operating lever is arranged to physically correspond with said at least one physical movement and indicate changes in the spatial arrangement of the system component.

2. The medical diagnostic device as claimed in claim 1, wherein the operating lever is congruent to the system component.

3. The medical diagnostic device as claimed in claim 1, wherein the operating lever has the form of the system component.

4. The medical diagnostic device as claimed in claim 1, wherein a direction of movement of the operating lever corresponds to a direction of movement of the system component.

5. The medical diagnostic device as claimed in claim 1, wherein a color of the operating lever corresponds to a color coding of the system component.

6. The medical diagnostic device as claimed in claim 1, wherein the operating element comprises an illumination device and a light color of the illumination device corresponds to a color coding of the system component.

7. The medical diagnostic device as claimed in claim 1, wherein the operating lever is selected from the group consisting of: a joystick, a slide switch, and a rotary lever.

8. The medical diagnostic device as claimed in claim 1, wherein the operating element is a foot operated switch.

9. The medical diagnostic device as claimed in claim 1, wherein the system component is a C arm and the operating lever for controlling the C arm has a form adapted to the C arm.

10. The medical diagnostic device as claimed in claim 9, wherein the operating lever for controlling the C arm comprises an operating knob being essentially shaped as a perpendicular round disk and cut off in a front region thereof.

11. The medical diagnostic device as claimed in claim 10, wherein a surface of the disk has a form of an elevation which is a characteristic of the C arm.

12. The medical diagnostic device as claimed in claim 1, wherein the system component is a panel and the operating lever for controlling the panel has a form adapted to the panel.

13. The medical diagnostic device as claimed in claim 12, wherein the operating lever for controlling the panel comprises an operating knob with a round base surface on which four perpendicular and unbowed elements are arranged at an edge of the base surface adapted to an edge of the panel.

14. The medical diagnostic device as claimed in claim 1, wherein the system component is a patient receiving table and the operating lever for controlling the patient receiving table has a form adapted to the patient receiving table.

15. The medical diagnostic device as claimed in claim 14, wherein the operating lever for controlling the patient receiving table comprises a toggle switch attached in a vertical position to the operating lever.

16. The medical diagnostic device as claimed in claim 1, further comprising a control computer connected to the system component.

17. The medical diagnostic device as claimed in claim 16, wherein the control computer comprises a tone generator that generates a tone and assigns the tone to the control system as an acoustic feedback.

18. The medical diagnostic device as claimed in claim 16, wherein the medical diagnostic device comprises a plurality of system components and a plurality of different tones differing in tone pitch or tone color are generated by the control computer and assigned to each of the system components or a control command for controlling the each of the system components.

19. A method for controlling a medical diagnostic device, comprising:
- coupling an operating element to a control computer;
- effecting with the operating element at least one physical movement in a system component of the medical diagnostic device to change a spatial arrangement of the system component;
- attaching an operating lever on the operating element, the operating lever comprising a structural characteristic indicative of a form of the system component; and
- arranging the structural characteristic of the operating lever to physically correspond with said at least one physical movement and indicating changes in the spatial arrangement of the system component.

* * * * *